United States Patent [19]

Kani et al.

[11] 4,370,033

[45] Jan. 25, 1983

[54] EYEBALL EXAMINING DEVICE

[75] Inventors: Kazutaka Kani, Motoryamanakamachi; Kuniomi Abe; Masahiko Konagaya, both of Kobe; Noboru Ono, Nishinomiya, all of Japan

[73] Assignee: Konan Camera Research Institute, Hyogo, Japan

[21] Appl. No.: 84,816

[22] Filed: Oct. 15, 1979

[51] Int. Cl.³ .......................... A61B 3/14; A61B 3/10; G03B 29/00
[52] U.S. Cl. .................................. 351/206; 351/211; 351/214; 351/221; 354/6 Z
[58] Field of Search .................... 351/6, 7, 9, 13, 14, 351/16; 354/62

[56] References Cited

U.S. PATENT DOCUMENTS 4,146,310 3/1979 Kohayakawa et al. ................ 351/7
4,196,979 4/1980 Kohayakawa et al. .............. 354/62
4,279,478 7/1981 Matsumura ........................... 351/13

Primary Examiner—John K. Corbin
Assistant Examiner—Rodney B. Bovernick
Attorney, Agent, or Firm—Eugene E. Geoffrey, Jr.

[57] ABSTRACT

An eye examining device having a television pickup camera, an optical system for magnifying the eye ground or retina and focussing the image on said camera, a television monitor connected to the camera to display the image of the retina and an optical pattern movably disposed in the plane of the image and a light source illuminating said pattern.

6 Claims, 1 Drawing Figure

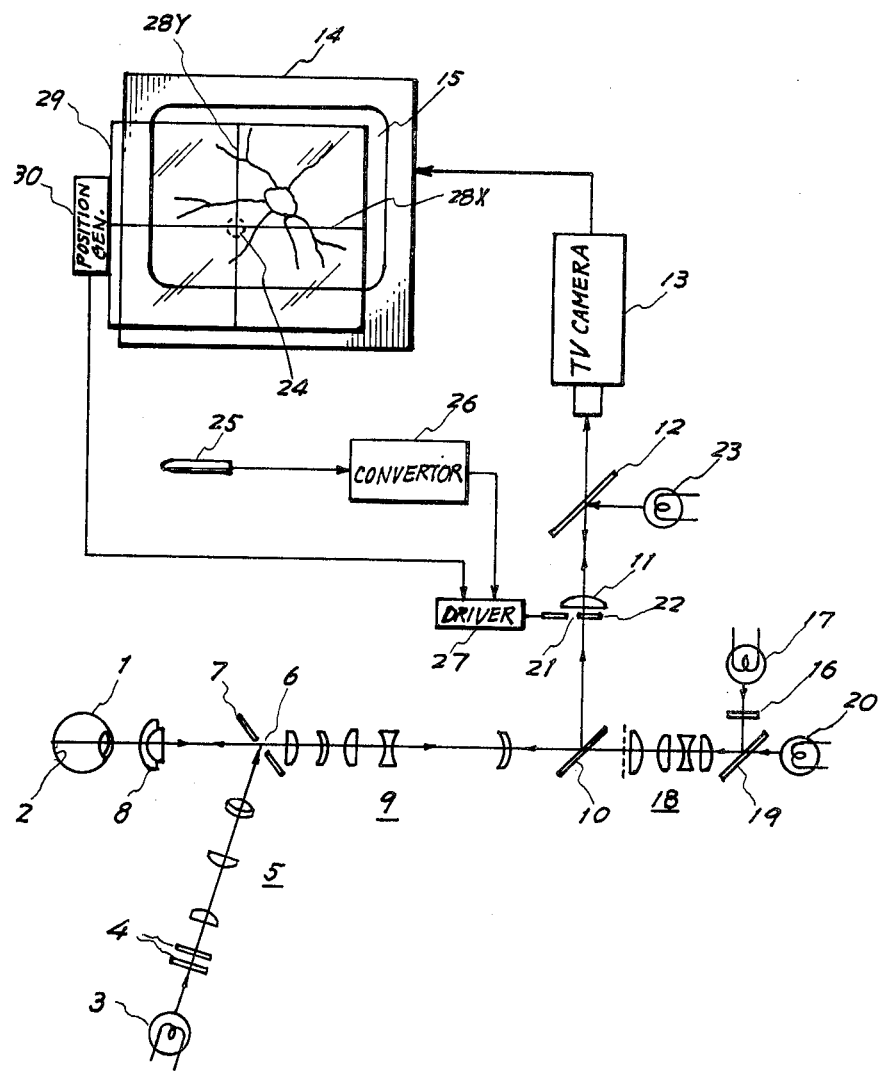

EYEBALL EXAMINING DEVICE

This invention relates to an eyeball examining device and more specifically a device for examining eye functions such as light sensitivity distribution over the eye ground or retina and eyeball motion by projecting a visible light beam onto various areas of the eye ground while observing a magnified image of the eye ground on an infrared ray television monitor.

Although such devices have been known as eye ground visual field testers or eyeball motion testers, it has been difficult to provide accurate correspondence of the magnified image with the area illuminated by the visible light beam. More particularly, it has been difficult to direct a visible light beam onto a small specific area of the eye ground which is designated in the eye ground image displayed on the monitor or, contrarily, to specify in the displayed eye ground image the area which is now illuminated by a visible light beam.

Accordingly, an object of this invention is to provide an eyeball examining device which can rapidly and accurately direct a light beam to any area of the eye ground by designating a corresponding area in a magnified monitoring image.

Another object of this invention is to provide an eyeball examining device which can also project an optical pattern other than the light spot onto the eye ground and, at the same time display the same pattern in superposition with the eye ground image displayed on the monitor.

According to the principle of this invention, the device comprises a television pick-up camera, a main optical system for magnifying an image of the eye ground or retina and coupling it to the television camera, an infrared ray source, means for directing an infrared ray beam from this source to the eye ground through a part of the main optical system and a television monitor for displaying the image picked up by the television camera. This invention further comprises an optical pattern located movably in the eye ground image plane of the main optical system and a light source for illuminating this pattern from the side of the television camera.

These and other objects and features of this invention will be described in more detail hereinunder with reference to the accompanying drawing.

IN THE DRAWING

The single drawing shows an embodiment of the device according to this invention.

In the drawing, an eye 1 having an eye ground or retina 2 to be examined is illuminated by a light source 3. The light from the light source 3 is filtered by an infrared ray filter 4 which allows only infrared rays to pass therethrough and the filtered infrared rays are directed onto the eye 1 through condenser lenses 5, a mirror 7 having a central hole 6 and a microscope objective 8 to illuminate the eye ground 2. The infrared rays reflected by the eye ground 2 are led through the objective 8, the central hole 6 of the mirror 7, imaging lenses 9 and a half-mirror 10 to form an infrared ray image of the eye ground 2. This image is picked up through an intermediate lens 11 and a half-mirror 12 by a television camera 13 and its magnified image is visibly displayed on the screen 15 of a television monitor 14.

The device also includes a fixed reference mark 16 which is illuminated by a visible light source 17. This mark is used for enabling the eye 1 to properly face to the device by looking hard at it through the objective 8, central hole 6, imaging lenses 9, half-mirror 10, imaging lenses 18 and a half-mirror 19. Another light source 20 is provided for projecting a weak visible light over the whole range of the eye ground 2 through the half-mirror 19, imaging lenses 18, half-mirror 10, imaging lenses 9, central hole 6 and objective 8 to provide a background with suitable brightness.

The arrangement as described above is common to known eye ground visual field testers according to the prior art, except for some differences in light path arrangement. In such prior art devices, a visible light beam is introduced from the outside into the above described light path to project a light spot onto the eye ground 2. The examiner may change position, brightness, size and the like of the light spot while adjusting brightness of the background light source 20 and inquire of the examinee as to whether he can see the light spot or not, thereby measuring sensitivities of various areas of the eye ground 2. However, the light spot could not be displayed clearly on the screen 15 of the monitor 14 and, therefore, it was difficult to obtain an accurate position of the light spot on the displayed image.

In the illustrated embodiment of this invention, an infrared ray filter 22 having a pin-hole 21 is located in the image plane in the main light path and illuminated by a visible light source 23 through the half-mirror 12. The image plane is a plane at which the image of eye ground is formed by the objective 8 and imaging lenses 9.

In this device, a monitoring image of the eye ground is displayed on the monitor screen 15 in the same manner as in the case of prior art devices, since the infrared ray filter 22 can pass infrared rays without any difficulty. When the light source 23 is turned off, the pin-hole 21 of the infrared ray filter 22 is displayed as a bright spot 24 on the monitoring image. This is due to some amount of infrared absorption of the infrared ray filter 22 itself.

Then, the infrared ray filter 22 is moved along the image plane, in a manner as described later, to locate the spot 24 at a desired position of the eye ground image on the screen 15. If the light source 23 is then turned on, a corresponding desired position of the eye ground 2 can be illuminated with a visible light beam. Thus, it is possible to effect more easily and accurately various examinations and tests than by the prior art devices, by changing brightness of the light source 23 and/or diameter of the pin-hole 21 of the filter 22.

Movement of the infrared ray filter 22 can be controlled most easily by utilizing a known light pen system. As shown in the drawing, a light pen 25 having a light sensing element at the tip is coupled through a signal convertor 26 to a filter driver 27. The signal convertor 26 serves to compare a signal output of the light pen 25 which is placed in contact with the monitor screen 15 with horizontal and vertical deflection sawtooth wave signals of the television camera 13 to convert it into X and Y positional signals. The driver 27 converts the positional signals into mechanical movement in X and Y directions to locate the pin-hole 21 of the filter 22 so that the light beam from the light source 23 can project a spot onto a corresponding area of the eye ground 2.

The illustrated embodiment includes another means of controlling movement of the filter 22, which comprises a transparent reference board 29 having orthogonal X and Y reference lines 28X and 28Y, which is supported movably in both X and Y directions by appropriate supporting means (not shown). The reference board 29 is coupled to a positional signal generator 30 which converts the mechanical movement of the reference board 29 into X and Y positional signals which in turn are supplied to the driver 27 to effect corresponding movement of the filter 22 in the same manner as above.

This device can also be utilized as an eyeball motion tester, when the light source 17 is turned off and the infrared ray filter 22 and accordingly the visible light spot from the pin-hole 21 is moved arbitrarily. The examiner may make the examinee to look hard at the moving spot and examine the motion of the eye ground following it.

It should be noted that, in the device of this invention, the infrared ray filter 22 is located in the image plane of the eye ground 2 which is picked up by the television camera 13. This results in accurate coincidence of the light spot position on both the actual eye ground 2 and its monitored image, regardless of any slight offset of the optical system or fluctuation in operation of the television camera and/or monitor due to variation in supply voltage.

While, in the above described embodiment, the infrared ray filter 22 having the pin-hole 21 was used for imaging a light spot on the eye ground 2 and monitor screen 15, this invention is not limited to this structure. For example, this device can be utilized for various tests and examination such as eyeball motion and variation in fixed visual point by using a suitable test pattern in place of the pin-hole 21. More specifically, frequency characteristic examination can be done with a striped pattern and vision test can be effected at any position of the eye ground by using a vision test chart. Furthermore, it has been found that these test patterns can be conventional color slides, being not always a special infrared ray filter. Using a color slide, the examinee can see a color image and a black-and-white image is displayed on the monitor screen 15 due to infrared permeability difference about colors. Moreover, when a pair of such devices are provided, it is possible to provide a function of the haploscope which can examine both eyes at the same time to effect examination of strabism and amblyopia.

What is claimed is:

1. An eyeball examining device, comprising a television pick-up camera, a main optical system including an image plane for focusing an eye ground image on said plane and on said television camera, an infrared ray source, means for directing infrared rays from said source to the eye ground and a television monitor for displaying the image picked up by said television camera, said device further comprising an optical infrared filter pattern located in the eye ground image plane of said main optical system, means for moving said pattern in said image plane and a light source for illuminating said optical pattern and imaging it on said eye ground for display on said television monitor.

2. A eyeball examining device according to claim 1 wherein said optical pattern includes an infrared ray filter having a pin-hole formed therein.

3. An eyeball examining device, comprising a television pick-up camera, a main optical system for focusing an eye ground image on said television camera, an infrared ray source, means for directing infrared rays from said source to the eye ground and a television monitor for displaying the image picked up by said television camera, said device further comprising an optical pattern located in the eye ground image plane of said main optical system, means for moving said pattern in said image plane and a light source for illuminating said optical pattern and imaging it on said eye ground for display on said television monitor, said moving means including means for cooperating with said television monitor and detecting the position thereof on the display screen of said monitor to produce a positional signal and driving means for positioning said optical pattern in accordance with said positional signal.

4. An eyeball examining device according to claim 3 wherein said positional signal producing means consists of a light sensing pen device for detecting its position on the television monitor and means responsive to said pen for positioning the optical pattern with reference to the eye ground.

5. An eyeball examining device according to claim 3 wherein said optical pattern includes an infrared ray filter having a pin-hole formed therein.

6. An eyeball examining device according to claim 5 wherein said positional signal producing means consists of a light sensing pen device.

* * * * *